US00PP36840P3

(12) United States Plant Patent
Akiba et al.

(10) Patent No.: US PP36,840 P3
(45) Date of Patent: Jul. 22, 2025

(54) STRAWBERRY PLANT NAMED 'Fukushima ST14Go'

(50) Latin Name: ***Fragaria ananassa* L.**
Varietal Denomination: Fukushima ST14Go

(71) Applicant: Fukushima Prefecture, Fukushima (JP)

(72) Inventors: Miho Akiba, Koriyama (JP); Satomi Miyashita, Shibukawa (JP)

(73) Assignee: FUKUSHIMA PREFECTURE (JP)

( * ) Notice: Subject to any disclaimer, the term of this patent is extended or adjusted under 35 U.S.C. 154(b) by 0 days.

(21) Appl. No.: 18/445,019

(22) Filed: Mar. 3, 2023

(65) Prior Publication Data

US 2024/0298557 P1 Sep. 5, 2024

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208
CPC ..... A01H 5/0893
See application file for complete search history.

*Primary Examiner* — Kent L Bell
(74) *Attorney, Agent, or Firm* — Kilpatrick Townsend & Stockton LLP

(57) ABSTRACT

'Fukushima ST14Go' is a new vigorous strawberry variety having an upright growth habit that can withstand cold temperatures. 'Fukushima ST14Go' has large, strong yellowish red, conical fruit having pale pink flesh.

5 Drawing Sheets

Genus and species: The strawberry plant of this invention is botanically known as *Fragaria ananassa* L.

Variety denomination: The variety denomination is 'Fukushima ST14Go'.

BACKGROUND

'Fukushima ST14Go' arose from a cross between maternal variety 'Kaorino' and paternal variety 'Tochiotome' performed in Koriyama city, Fukushima prefecture, Japan in 2012. The plant was first asexually reproduced in Koriyama city, Fukushima prefecture by runners. 'Fukushima ST14Go' was selected from 162 individuals in 2014. The characteristics of 'Fukushima ST14Go' are stable over subsequent asexual reproduction by runners.

Field tests were conducted in six locations (Date City, Sukagawa City (2 locations), Kagamiishi Machi, Tanagura Machi, and Iwaki City) in 2018; four locations (Sukagawa City (2 locations), Aizuwakamatsu City and Iwaki City) in 2019, three locations (Aizuwakamatsu City, Okuma Machi, and Iwaki City) in 2020 and seven locations (Date City, Tanagura Machi, Aizuwakamatsu City (2 locations), Soma City, Okuma Machi, and Iwaki City) in 2021.

BRIEF SUMMARY

'Fukushima ST14Go' is maintained by asexual propagation by runners in Fukushima, Japan. 'Fukushima ST14Go' has an upright growth habit; and large, strong yellowish red, conical fruit that has pale pink flesh. The type of bearing is non-remontant. 'Fukushima ST14Go' can be distinguished from parent varieties 'Kaorino' (unpatented) and 'Tochiotome' (unpatented) as shown in Table 1. 'Tochiotome' is a close comparison variety.

Colors are designated with reference to The Royal Horticultural Society (R.H.S.) Colour Chart, 1995.

TABLE 1

Comparison of 'Fukushima ST14Go' to Parental Cultivars.

| Name of Similar Variety | Characteristics | Characteristic of Similar Variety | Characteristic of Variety of Application |
|---|---|---|---|
| 'Kaorino' | Plant: vigor | moderately strong | strong |
| | relative intensity of color of upper side of leaf | | darker than 'Kaorino' |
| | Fruit: color of core | White 155B | Light Red 33C |
| 'Tochiotome' | Plant: growth habit | semi-upright | upright |
| | Fruit: color | Brilliant red 45A | strong Yellowish Red 44A |
| | Fruit: position of achenes | deep below surface | level with surface |

BRIEF DESCRIPTION OF THE DRAWINGS

The colors in the photograph are depicted as nearly true as is reasonably possible to obtain in color reproductions of this type. The photographs were obtained from plants of less than one year of age. Seedlings were started in July, planted in September and grown until April.

DETAILED DESCRIPTION

Characteristics of 'Fukushima ST14Go'

The plant growth habit is upright. The plant diameter is 38.2 cm. The plant vigor is strong and is maintained without lighting even in the severe cold period (Table 2). The generation of side buds is rare and the fruit cluster is slightly long and hard to break, so the work efficiency is excellent.

Figure 1:
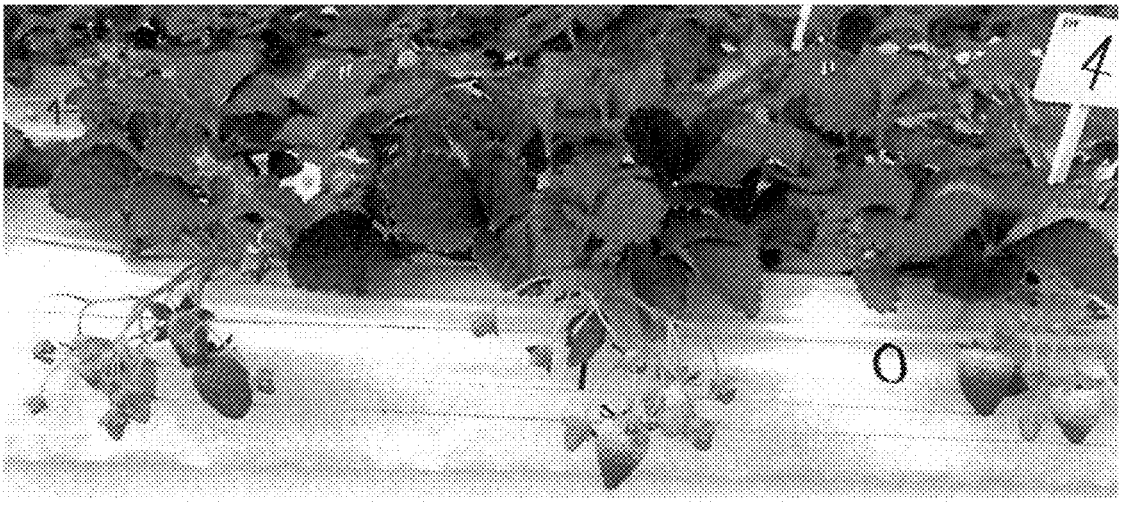
FIG. 1 depicts plants of 'Fukushima ST14Go' grown in a glass greenhouse in Fukushima, Japan.
Figure 2:
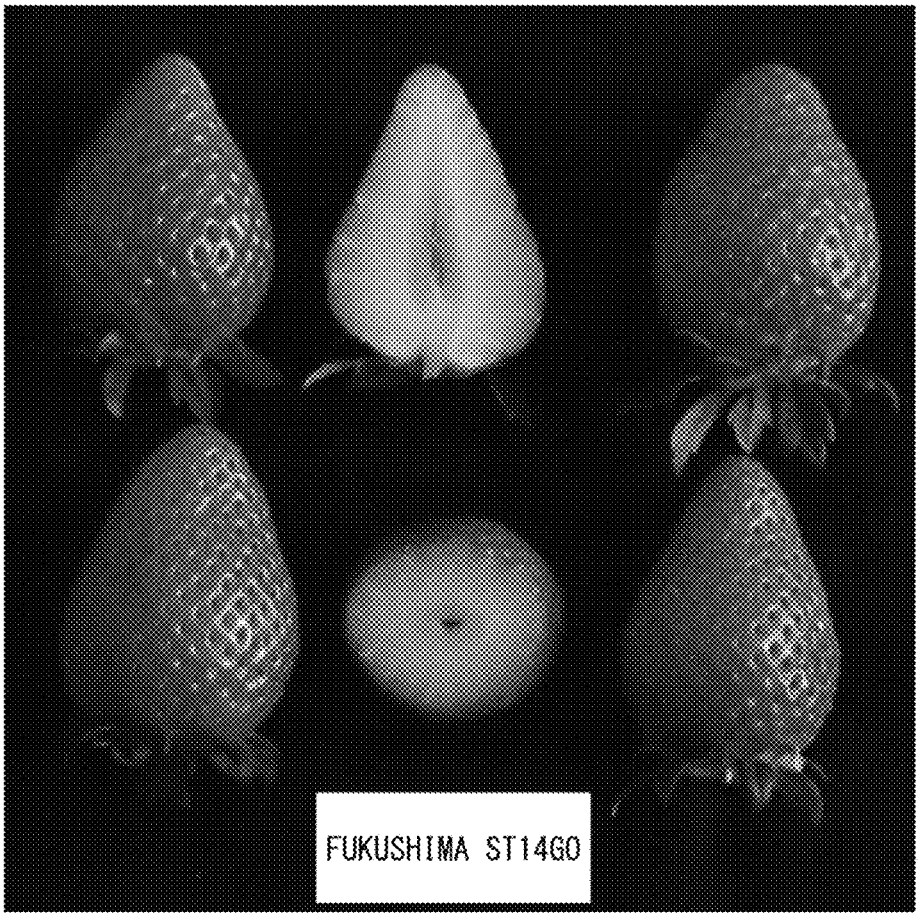
FIG. 2 shows exterior and interior of representative fruit of 'Fukushima ST14Go'.
Figure 3:
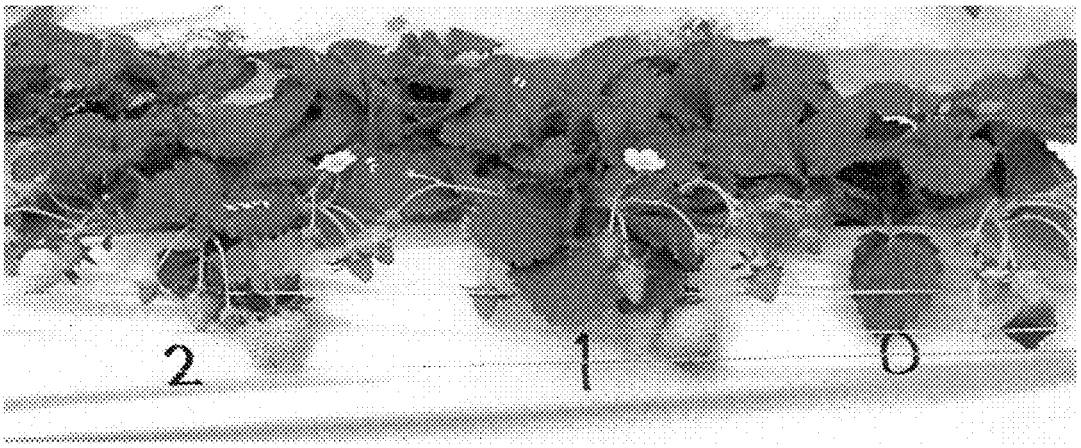
FIG. 3 depicts plants of comparison variety 'Tochiotome' grown in a glass greenhouse in Fukushima, Japan.
Figure 4:
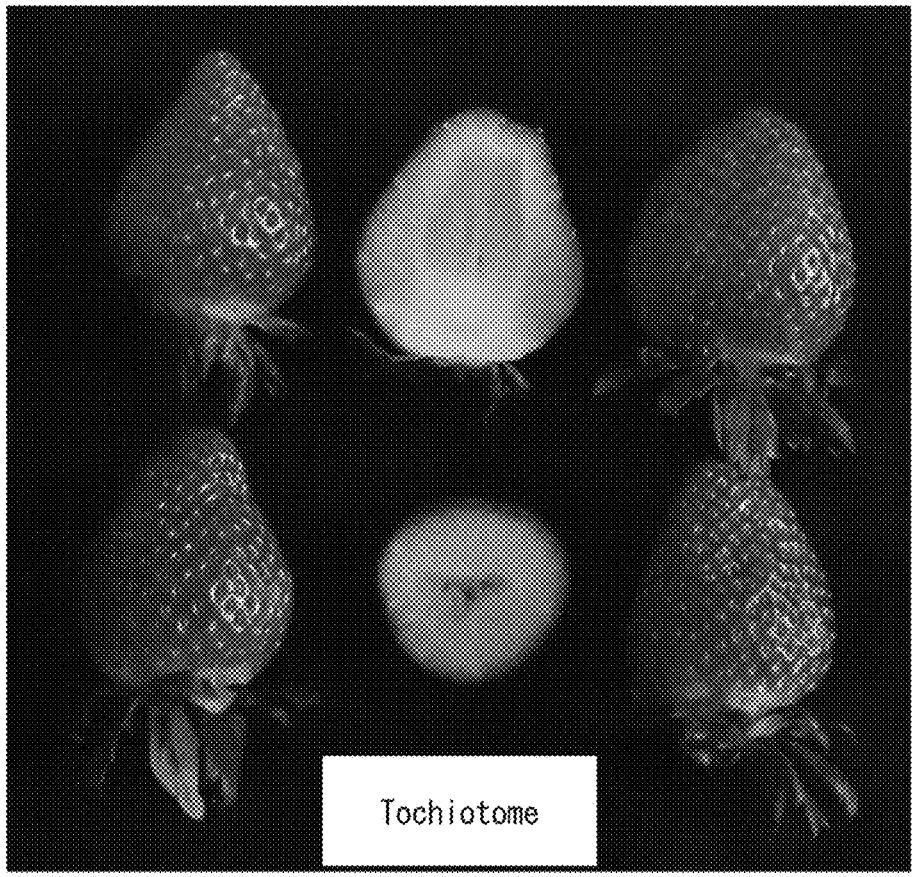
FIG. 4 shows exterior and interior of representative fruit of comparison variety 'Tochiotome'.
Figure 5:
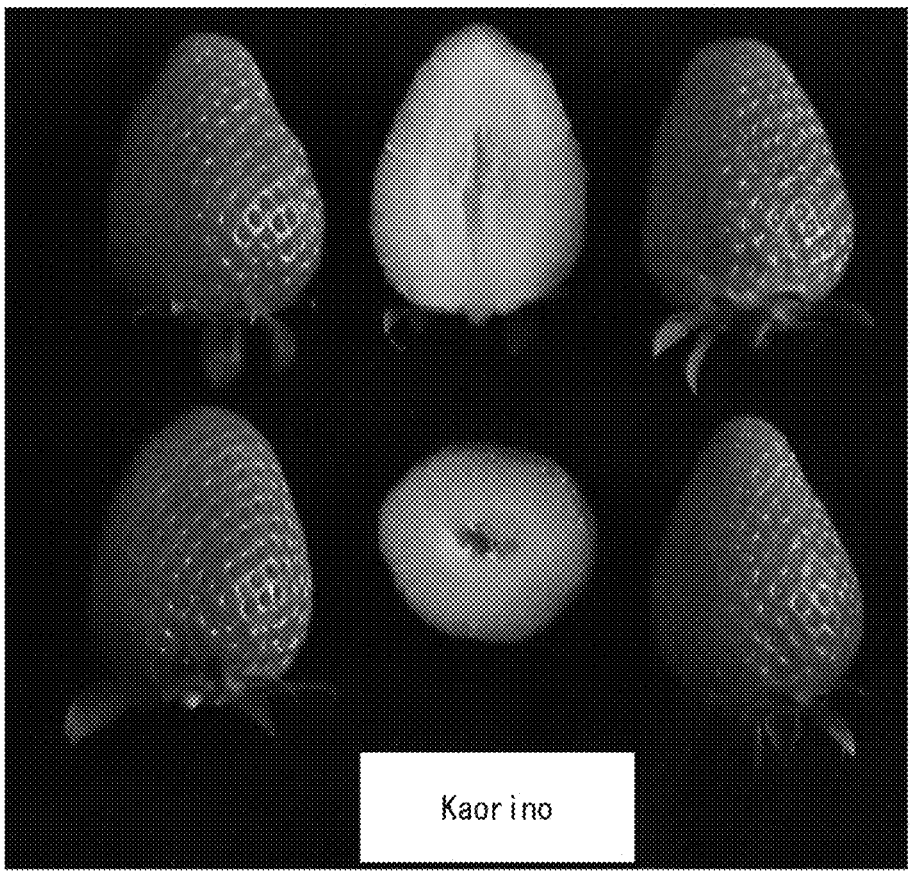
FIG. 5 shows exterior and interior of representative fruit of comparison variety 'Kaorino'.

The fruit shape is conical, and the fruit color is strong yellowish red (FIG. 1, Table 7). Fruit are long and narrow, which is the same as 'Tochiotome'. The following characteristics of 'Fukushima ST14Go' fruit are also the same as 'Tochiotome': 'Fukushima ST14Go' exhibits medium adhesion of calyx to fruit; the position of the calyx in relation to the fruit is flat; and the color uniformity is weak. The stalk length of 'Fukushima ST14Go' is 25.9 cm compared to 21.9 cm for 'Tochiotome'.

'Fukushima ST14Go' has 4.5 stolons compared to 3.9 stolons for 'Tochiotome'. Stolon length is 60.9 cm and the diameter is 2.1 mm. Stolon color is Greyed-Purple 185A 'Fukushima ST14Go' has the following foliage characteristics compared to 'Tochiotome'. The length is 7.2 cm compared to 6.0 cm for 'Tochiotome'; the length and width of apical lobes is 1.28 compared to 1.24 for 'Tochiotome'; and the leaf area is 107.2 $cm^2$ compared to 82.0 $cm^2$ for 'Tochiotome'. The basal shape, acute, is the same as 'Tochiotome'. Both cultivars have medium surface roughness as determined on a transverse section of the leaf and strong surface gloss on the upper surface of the leaf. Both also have serration of the tip; and a transverse section shape that is curved upward. The third unfolded leaf has a diameter of 19.4 cm and a width of 5.6 cm. Serration of the tip is medium. There are 3 leaflets. The number of teeth on the terminal leaflet is 19. The upper surface of the leaf is Green 137A and the lower surface is Green 139D.

Petioles are 9.1 cm compared to 5.6 cm for 'Tochiotome'. The petiole diameter of 'Fukushima ST14Go' is 3.6 mm and the color is Yellow green 144C. The petiolule is 1.3 cm in length with a diameter of 3.0 mm. The color is Yellow-green 144C.

There are 2 stipules. Stipule length is 1.9 cm and 1.2 mm. The color is Green 137A Flowers of 'Fukushima ST14Go' have 5 petals and are of medium diameter, both of which are the same as 'Tochiotome'.

The root development for 'Fukushima ST14Go' was generally increased compared to 'Tochiotome'. When seedlings were placed in water for three weeks, the number of roots for 'Fukushima ST14Go' was 13.9 compared to 12.9 for 'Tochiotome'; the maximum root length was 5.1 cm for 'Fukushima ST14Go' compared to 4.4 cm for 'Tochiotome'; and the roots of 'Fukushima ST14Go' were finer than those of 'Tochiotome'.

Harvesting starts early and yields are high by the end of the year. The percentage of large fruits is high and there are few malformed fruits. The taste is good, the sugar content is high, and skin firmness is high (Tables 4 to 7).

Evaluation in Field Tests

Field tests provided the following additional characteristics. The plant vigor was maintained even in the severe cold period (common). Yields were high (Sukagawa). The taste was good with little variation in taste from season to season. Damage was not noticeable after harvest. The tail fruit of each fruit cluster appeared small.

In view of the vigor of the variety, it is expected that 'Fukushima ST14Go' can be cultivated throughout the Fukushima prefecture as well as corresponding areas that have similar cold periods.

The development of clusters may be delayed after the second cluster is harvested. The top fruit is large, but bottom fruit tends to become smaller.

'Fukushima ST14Go' has moderate to weak resistance to Antrhacnose and weak resistance to chlorosis. Pest control can be carried out in the same manner as the practice for 'Tochiotome'.

Fruit hardiness and pulp hardness decreased more than that of 'Tochiotome' 2 and 4 days after harvest, and post-harvest storability was inferior to that of 'Tochiotome'. In Japan, shipping is possible from about November to June.

Table 2. Comparison of 'Fukushima ST14Go' and parental cultivar growth characteristics at start of harvest (December 2020, without lighting, Fukushima) of plants less than one year of age. Seedling were started in July, planted in September, and grown until April.

| Variety | Plant growth habit | Plant vigor | Plant height (cm) | Petiole length (cm) | Leaflet length (cm) | Terminal inflorescence length (cm) |
|---|---|---|---|---|---|---|
| 'Fukushima ST14Go' | upright | strong | 23.1 | 9.1 | 7.2 | 25.9 |
| 'Tochiotome' (standard) | semi-upright | medium | 14.1 | 5.6 | 6.0 | 21.9 |
| 'Kaorino' (reference) | upright | strong | 23.4 | 11.1 | 7.9 | 39.9 |

TABLE 3

Comparison of 'Fukushima ST14Go' and parental cultivar flowering and harvest dates (November 2020 to May 2021, Fukushima)

| | Terminal inflorescence | | | Second inflorescence | | |
|---|---|---|---|---|---|---|
| Variety | Flowering date | Harvest date | No. of flowers | Flowering date | Harvest date | No. of flowers |
| 'Fukushima ST14Go' | 11/10 | 12/17 | 14.1 | 12/20 | 2/1 | 11.4 |
| 'Tochiotome' (standard) | 11/14 | 12/28 | 15.7 | 1/5 | 2/23 | 11.5 |
| 'Kaorino' (reference) | 11/4 | 12/10 | 12.9 | 12/6 | 1/19 | 13.0 |

| | Third inflorescence | | | Fourth inflorescence | | |
|---|---|---|---|---|---|---|
| Variety | Flowering date | Harvest date | No. of flowers | Flowering date | Harvest date | No. of flowers |
| 'Fukushima ST14Go' | 2/27 | 3/31 | 7.1 | 4/13 | 5/11 | 10.0 |
| 'Tochiotome' (standard) | 3/15 | 4/19 | 8.0 | 4/14 | 5/16 | 9.6 |
| 'Kaorino' (reference) | 2/9 | 3/16 | 8.1 | 3/5 | 4/8 | 7.1 |

TABLE 4

Comparison of 'Fukushima ST14Go' and parental cultivar fruit production by month1 (November 2020 to May 2021, Fukushima)

| Variety | November No. | November Yield (g) | December No. | December Yield (g) | January No. | January Yield (g) | February No. | February Yield (g) |
|---|---|---|---|---|---|---|---|---|
| 'Fukushima ST14Go' | 0.1 | 1.6 | 3.5 | 88.8 | 7.0 | 109.4 | 5.8 | 106.3 |
| 'Tochiotome' (standard) | 0.0 | 0.0 | 0.7 | 24.6 | 7.4 | 130.8 | 3.5 | 67.3 |
| 'Kaorino' (reference) | 0.0 | 0.0 | 3.2 | 98.0 | 7.3 | 124.1 | 5.6 | 95.0 |

| Variety | March No. | March Yield (g) | April No. | April Yield (g) | May No. | May Yield (g) | Total[1)] No. | Total[1)] Yield (g) |
|---|---|---|---|---|---|---|---|---|
| 'Fukushima ST14Go' | 2.7 | 45.7 | 5.2 | 81.2 | 5.4 | 105.6 | 29.7 | 538.7 |
| 'Tochiotome' (standard) | 4.1 | 63.5 | 6.9 | 119.1 | 4.7 | 95.5 | 27.3 | 500.6 |
| 'Kaorino' (reference) | 2.8 | 67.3 | 7.6 | 118.8 | 7.1 | 105.8 | 33.6 | 609.0 |

[1)]fruit of 6.0 g or greater (excluding malformed fruit)

TABLE 5

Comparison of 'Fukushima ST14Go' and parental cultivar yield characteristics per plant (November 2020 to May 2021, Fukushima)

| | On-specification yield[1)] | | | | | | | |
|---|---|---|---|---|---|---|---|---|
| | 3L (≥25 g) | | 2L (≥17 g) | | L (≥ 12 g) | | M/S (≥ 6 g) | |
| Variety | No. | Yield (g) | No. | Yield (g) | No. | Yield (g) | No. | Yield (g) |
| 'Fukushima ST14Go' | 6.9 | 230.9 | 6.8 | 138.5 | 5.4 | 77.1 | 10.7 | 92.2 |
| 'Tochiotome' (standard) | 5.6 | 190.0 | 6.7 | 139.9 | 6.6 | 94.8 | 8.4 | 76.0 |
| 'Kaorino' (reference) | 7.7 | 263.6 | 7.4 | 153.9 | 6.1 | 87.1 | 12.3 | 104.4 |

| | Off-specification yield | | | | | |
|---|---|---|---|---|---|---|
| | Malformed fruit[2)] | | Offal fruit[3)] | | Total | |
| Variety | No. | Yield (g) | No. | Yield (g) | No. | Yield (g) |
| 'Fukushima ST14Go' | 1.2 | 21.0 | 4.4 | 20.2 | 35.3 | 579.9 |
| 'Tochiotome' (standard) | 2.9 | 67.9 | 2.6 | 10.9 | 32.8 | 579.4 |
| 'Kaorino' (reference) | 4.2 | 83.6 | 8.1 | 32.9 | 45.9 | 725.5 |

[1)]fruit of 6.0 g or greater (excluding malformed fruit)
[2)]malformed fruit of 6.0 g or greater
[3)]fruit of less than 6.0 g

TABLE 6

Comparison of 'Fukushima ST14Go' and parental cultivar fruit production characteristics (November 2020 to May 2021, Fukushima).

| Variety | Avg. fruit weight[1)] (g) | Product fruit ratio[2)] (%) | Irregular shaped fruit ratio[3)] (%) | Fruit firmness[4)] (gf) December Skin | December Flesh | January Skin | January Flesh |
|---|---|---|---|---|---|---|---|
| 'Fukushima ST14Go' | 18.2 | 84.1 | 4.8 | 105.0 | 22.9 | 140.4 | 52.0 |
| 'Tochiotome' (standard) | 18.3 | 83.4 | 4.6 | 151.9 | 38.1 | 118.5 | 55.5 |
| 'Kaorino' (reference) | 17.8 | 71.5 | 8.8 | 97.0 | 38.5 | 103.3 | 32.2 |

| | Fruit firmness[4)] (gf) | | | | | |
|---|---|---|---|---|---|---|
| | February | | March | | April | |
| Variety | Skin | Flesh | Skin | Flesh | Skin | Flesh |
| 'Fukushima ST14Go' | 125.6 | 36.2 | 148.9 | 43.8 | 106.6 | 48.0 |
| 'Tochiotome' (standard) | 118.7 | 40.7 | 124.6 | 60.3 | 84.8 | 36.6 |
| 'Kaorino' (reference) | 124.7 | 31.9 | 152.4 | 54.6 | 87.9 | 28.3 |

| | Fruit firmness[4)] (gf) | | | |
|---|---|---|---|---|
| | May | | Avg. | |
| Variety | Skin | Flesh | Skin | Flesh |
| 'Fukushima ST14Go' | 91.9 | 32.4 | 119.7 | 39.2 |
| 'Tochiotome' (standard) | 65.9 | 21.5 | 110.7 | 42.1 |
| 'Kaorino' (reference) | 82.3 | 33.9 | 107.9 | 36.6 |

[1)]Product fruit weight/product fruit number
[2)]Product fruit number/total fruit number × 100
[3)]Irregular shaped fruit number/product fruit number × 100 (*product fruit: fruit of 6.0 g or greater excluding malformed fruit)
[4)]measured by a creepmeter (YAMADEN, RE2-3305S), penetration resistance to a 3 mm dia. cylindrical plunger penetrated at a maximum rate of 1 mm/sec.

TABLE 7

Comparison of 'Fukushima ST14Go' and s parental cultivar fruit quality characteristic (November 2020 to May 2021, Fukushima).

| Variety | Fruit shape[1)] | Skin color[1)] | Sugar content[2)] (% Brix) December | January |
|---|---|---|---|---|
| 'Fukushima ST14Go' | conical | Strong Yellowish Red 44A | 11.7 | 9.3 |
| 'Tochiotome' (standard) | conical | Vivid Red 45A | 11.0 | 9.3 |
| 'Kaorino' (reference) | conical | Strong Yellowish Red 44A | 9.2 | 9.1 |

TABLE 7-continued

Comparison of 'Fukushima ST14Go' and s parental cultivar fruit quality characteristic (November 2020 to May 2021, Fukushima).

| Variety | Sugar content[2)] (% Brix) | | | |
|---|---|---|---|---|
| | February | March | April | May |
| 'Fukushima ST14Go' | 11.2 | 10.6 | 12.1 | 10.8 |
| 'Tochiotome' (standard) | 10.9 | 11.2 | 10.3 | 9.6 |
| 'Kaorino' (reference) | 10.6 | 11.1 | 9.3 | 10.2 |

| Variety | Acidity[2)] (%) | | |
|---|---|---|---|
| | December | January | February |
| 'Fukushima ST14Go' | 0.49 | 0.41 | 0.48 |
| 'Tochiotome' (standard) | 0.53 | 0.43 | 0.47 |
| 'Kaorino' (reference) | 0.42 | 0.34 | 0.44 |

TABLE 7-continued

Comparison of 'Fukushima ST14Go' and s parental cultivar fruit quality characteristic (November 2020 to May 2021, Fukushima).

| Variety | Acidity[2)] (%) | | |
|---|---|---|---|
| | March | April | May |
| 'Fukushima ST14Go' | 0.47 | 0.63 | 0.68 |
| 'Tochiotome' (standard) | 0.50 | 0.60 | 0.69 |
| 'Kaorino' (reference) | 0.45 | 0.48 | 0.56 |

[1)]at the time of investigation in January

[2)]measured by a strawberry Brix meter (ATAGO. PAL-BX/ACID4)

What is claimed is:

1. A new and distinct cultivar of strawberry plant substantially as described and illustrated herein.

* * * * *